(12) United States Patent
Moisan et al.

(10) Patent No.: US 7,695,673 B2
(45) Date of Patent: Apr. 13, 2010

(54) PROCESSES AND DEVICES FOR STERILIZING CONTAMINATED OBJECTS

(76) Inventors: Michel Moisan, 101 Avenue Beloeil, Outremont, Québec (CA) H2V 2Z1; Nicolas Philip, 6 Lotissement Pégasse, Beaumont-lès-Valence (FR); Bachir Saoudi, 2092, rue Hampton, Montréal, Québec (CA) H4A 2K3

( * ) Notice: Subject to any disclaimer, the term of this patent is extended or adjusted under 35 U.S.C. 154(b) by 1023 days.

(21) Appl. No.: 11/044,998

(22) Filed: Jan. 26, 2005

(65) Prior Publication Data

US 2005/0158206 A1    Jul. 21, 2005

Related U.S. Application Data

(63) Continuation-in-part of application No. PCT/CA03/01116, filed on Jul. 24, 2003.

(30) Foreign Application Priority Data

Jul. 26, 2002    (CA) .................................. 2395659

(51) Int. Cl.
*A61L 9/00* (2006.01)
*A61L 2/00* (2006.01)
*A62B 7/08* (2006.01)
*G01N 23/00* (2006.01)
*C25B 5/00* (2006.01)

(52) U.S. Cl. .................. 422/22; 422/1; 422/4; 422/21; 422/24; 422/119; 422/121; 422/186.04; 422/305; 422/906; 422/907; 250/455.11; 204/155

(58) Field of Classification Search .................... 422/1, 422/4, 21–22, 24, 119, 121, 186.04, 305, 422/906–907; 250/455.11; 204/155
See application file for complete search history.

(56) References Cited

U.S. PATENT DOCUMENTS

| | | | |
|---|---|---|---|
| 3,948,601 A | 4/1976 | Fraser et al. | |
| 4,643,876 A | 2/1987 | Jacobs et al. | |
| 5,325,020 A * | 6/1994 | Campbell et al. | ...... 315/111.21 |
| 5,413,759 A | 5/1995 | Campbell et al. | |
| 5,482,684 A * | 1/1996 | Martens et al. | ............. 422/119 |
| 5,512,244 A * | 4/1996 | Griffiths et al. | ............... 422/23 |
| 6,019,801 A | 2/2000 | Gauthier et al. | |
| 2002/0172780 A1 | 11/2002 | Halverson | |
| 2005/0269199 A1 | 12/2005 | Pollak et al. | |

FOREIGN PATENT DOCUMENTS

| | | |
|---|---|---|
| EP | 1 084 713 A1 | 3/2001 |
| FR | 2 654 000 A1 | 5/1991 |
| WO | WO 00/72889 A1 | 12/2000 |

* cited by examiner

*Primary Examiner*—Jill Warden
*Assistant Examiner*—Monzer R Chorbaji
(74) *Attorney, Agent, or Firm*—Christensen O'Connor Johnson Kindness PLLC

(57) ABSTRACT

The present invention relates to a process for sterilizing a contaminated object. The process comprises the insertion of the object in a sterilization chamber having at least one discharge tube in communication therewith. Then, the tube is fed with a liquid or gas stream, and the stream is subjected to an electric field so as to generate a plasma, thereby exposing the contaminated object to the action of sterilizing species that are present in a post-discharge zone or in a zone of excitation of the plasma. A device for carrying such a process is also provided.

39 Claims, 13 Drawing Sheets

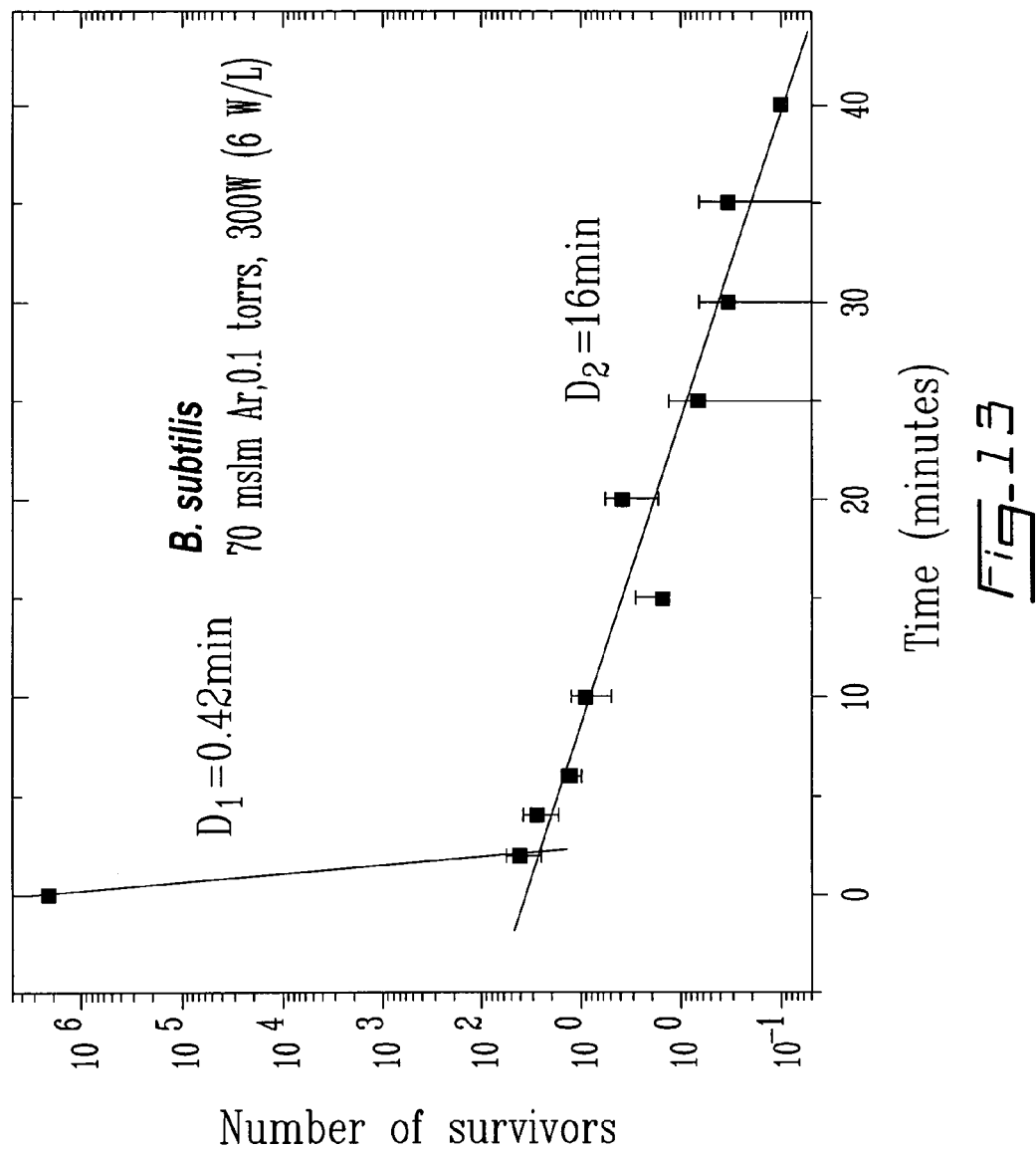

PROCESSES AND DEVICES FOR STERILIZING CONTAMINATED OBJECTS

CROSS-REFERENCE TO RELATED APPLICATIONS

The present application is a continuation-in-part of PCT International Patent Application No. PCT/CA2003/001116, filed on Jul. 24, 2003, which claims priority on Canadian Patent Application No. 2,395,659, filed on Jul. 26, 2002. Each of the above-mentioned applications are incorporated herein by reference in its entirety.

TECHNICAL FIELD

The present application relates to devices and processes allowing sterilization of contaminated objects. In particular, the present invention relates to high performance devices and processes for sterilizing contaminated objects, such as medical instruments and accessories, by utilizing a plasma gas, also called ionized gas. These processes and devices can carry out sterilization of an important surface of contaminated objects, in a single treatment.

BACKGROUND OF THE INVENTION

By reason of standards that are more and more rigid for the sterilization of objects, such as in the medical field and the food industry, there is an increasing need for new high performance devices and processes that are free of the limitations and/or disadvantages of known devices.

The devices that use plasma sterilizing processes, in spite of their excellent performances, have not yet achieve a significant breakthrough in the sterilization market that traditionally involves the utilization of devices that use vapor and/or chemical treatments.

U.S. Pat. No. 6,707,254 describes a sterilization process that uses a plasma post-discharge, this discharge being carried out in a gas mixture, in which the main gas is nitrogen, or argon. Such a mixture is described as advantageously containing between 0.5% and 20% $O_2$, in order that sterilization time be as short as possible.

The effect of UV on DNA has been studied in an article by Moisan et al., which appeared in International Journal of Pharmaceutics, vol. 226 pp 1-21 (2001).

These prior art processes have limitations, for example with respect to the homogeneity of distribution of sterilizing species and, consequently with respect to contaminated objects, and with respect to the total surface of the contaminated objects that can be treated in the same chamber.

Moreover, several of the known processes and devices tend to damage or deteriorate the objects to be sterilized. After being submitted to a plurality of such treatments these objects can be considerably damaged.

There was therefore a need for new processes and devices that are free of at least one limitation of the devices of the prior art.

SUMMARY OF THE INVENTION

It is therefore an object of the present invention to overcome the above-mentioned drawbacks and to provide new processes and devices for sterilizing contaminated objects.

According to a first aspect of the invention, there is provided a process for sterilizing a contaminated object in a sterilization chamber that is provided with at least one discharge tube. The discharge tube(s) reach(es) the sterilization chamber and is (are) fed with a liquid or gas stream feed. The contaminated object is subjected in the sterilization chamber to the action of sterilizing species that are present in a post-discharge zone or in a zone of plasma excitation that is generated, at the level of the discharge tube(s), by subjecting the stream to an electric field. The stream is adjusted by controlling the flow rate and/or the gas pressure in the chamber, so as to maximize Ultra Violet (UV) radiation intensity.

According to a second aspect of the invention, there is provided a process for sterilizing a contaminated object comprising:
  inserting the object in a sterilization chamber having at least one discharge tube in communication therewith,
  feeding the tube with a liquid or gas stream, and submitting the stream to an electric field so as to generate a plasma, thereby exposing the contaminated object to the action of sterilizing species that are present in a post-discharge zone or in a zone of excitation of the plasma,
  wherein the stream is adjusted by controlling its flow rate and/or gas pressure in the chamber, so as to maximize Ultra Violet (UV) radiation intensity.

It has been found that a process, as defined in the first or second aspect of the invention, for sterilizing a contaminated object by maximizing the UV radiation intensity through the control of the flow rate and/or gas pressure in the chamber, permit to obtain improved results with respect to the sterilization. In fact, such processes have demonstrated a high performance sterilization. It has been demonstrated, for a particular gas, that by obtaining a preferred range of values of pressure (that permit to maximize the UV radiation intensity) by measuring (recording) the UV emission intensity as a function of the pressure, and/or by obtaining a preferred range of values of flow rate (that permit to maximize the UV radiation intensity) by measuring the UV emission intensity as a function of the flow rate, and by applying at least one range (and preferably both ranges) of these values (ranges of pressure and flow rate) during a sterilization process, permit to optimize the sterilization process. In fact, by applying these preferred ranges of pressure and of flow rate, which each correspond to maximized values of UV radiation intensity, the time required for obtaining sterility of the contaminated object can be considerably reduced.

According to a third aspect of the invention, there is provided a process for sterilizing a contaminated object in a sterilization chamber provided with at least one discharge tube. The discharge tube(s) is in communication with the sterilization chamber and is (are) supplied with a liquid or gas stream. The contaminated object is subjected in the sterilization chamber to the action of sterilizing species that are present in a post-discharge zone or in a zone of plasma excitation that is generated at the level of the discharge tube(s) by treating the stream in an electric field. The ratio R=(CDT)/(CSC), wherein CDT represents the cross-section of the discharge tube in communication with the sterilization chamber or the sum of the cross-sections of the discharge tube(s). CSC represents the cross-section of the sterilization chamber (CSC), confirms the relation 0.05<R<0.70. The stream is adjusted by controlling the flow rate and/or gas pressure in the chamber, so as to maximize Ultra Violet (UV) radiation intensity.

It has been found that the process as defined in the third aspect of the invention was very effective for sterilizing a contaminated object. In fact, by maximizing the UV radiation intensity through control of the flow rate and/or gas pressure in the chamber, and by obtaining a ratio (CDT)/(CSC) comprised between 0.05 and 0.70, improved results with respect to the sterilization process were noted.

According to a fourth aspect of the invention, there is provided a process for sterilizing a contaminated object comprising:

inserting the object in a sterilization chamber having at least one discharge tube in communication therewith, feeding the tube with a liquid or gas stream, and subjecting the stream to an electric field so as to generate a plasma, thereby exposing the contaminated object to the action of sterilizing species that are present in a post-discharge zone or in a zone of excitation of the plasma, wherein the stream consists of helium, neon, argon, krypton, xenon, or mixtures thereof.

It has been found that by using a process as defined in the fourth aspect of the invention a high performance sterilization is obtained and deterioration or erosion of the treated object is considerably reduced. In fact, by using a gas stream consisting of helium, neon, argon, krypton, xenon, or mixtures thereof, the presence of oxidizing species being avoided, thereby considerably reducing damages that can be brought to the treated object. The person skilled in the art would clearly recognize that the expression "consists of" (or "consisting of") when referring, as example, to a particular gas means that this particular gas is the only one used in the process. In fact, in such a case the particular gas is used as provided from a supplier. The person skilled in the art would also understand that there may be some minor impurities contained in the gas provided from the supplier. However, it is preferable to use high purity grade gases in such process. It is also possible to use or prepare a mixture of more than one particular gas provided by a supplier. The term "pure", as used herein when referring to a particular gas, is used as a synonym of the expression "consists of" ("or consisting of").

According to another aspect of the invention, there is provided a sterilization device allowing the implementation of one of the processes as previously defined, comprising a source of plasma associated with one of the walls of the sterilization chamber by means of at least one discharge tube in which there is injected a gas or a mixture of gases eventually producing the plasma. The chamber comprises the object to be sterilized, and a vacuum pump carries the gases in the chamber and maintains therein a reduced pressure. The source of plasma also comprises an electric field applicator. The ratio R=(CDT)/(CSC), in which (CDT) represents the cross-section of the discharge tube or the sum of the cross-sections of the discharge tube(s) in communication with the sterilization chamber and (CSC) represents the cross-section of the sterilization chamber (CSC), confirms the relation 0.05<R<07.

It has been found that such a device permits to efficiently carry out any of the processes previously defined.

In the processes of the invention, the plasma generating electric field is preferably a high frequency field. For example, the frequency can be from about 10 Megahertz to about 3 Gigahertz. The frequency can be preferably of about 100 and to about 2450 MHz, and more preferably at 433, 915 or 2450 MHz which are frequencies authorized for industrial, medical and scientific (ISM) purposes), The gas stream flow rate can be adjusted to a value that is between 10 and 5000 standard cm$^3$ per minute (sccm), and preferably to a value between 50 and 3000 sccm. Advantageously, the pressure that is generated inside the sterilization chamber is between 0.05 and 10 torrs or 0.1 and 10 torrs. Alternatively, a pressure between 0.1 and 4 torrs or between 1 and 8 torrs can be used for certain gases. The steps of such processes can involve a pulsed gas in an electric field that is applied continuously, a pulsed electric field in a continuous gas stream, a pulsed gas in a synchronously pulsed electric field, a gas change or a combination thereof. The sterilizing species can comprise photons, radicals, atoms, molecules or combination thereof. Preferably, the sterilizing species comprise a major portion of photons and/or radicals. The object to be treated can be contaminated with micro-organisms such as viruses, spores, bacteria, fungi, molds, prions or combination thereof.

The processes of the present invention can be carried out at a temperature inside the sterilization chamber of 60° C. or less and preferably 50° C. or less. More preferably, this temperature is about 30° C. These processes can lasts between 10 minutes and 4 hours. They can be carried out in isolated or repeated manner in a multi-step sequential procedure.

In the processes according to the first, second and third aspects of the invention, the gas stream can comprise at least one component selected from the group consisting of molecular oxygen, nitrogen, neon, argon, krypton, xenon, helium, oxygen, carbon monoxide, carbon dioxide, $N_2O$, gases of formula $NO_x$ wherein x represents 1, 2 or 3, air, and mixtures thereof. According to a preferred embodiment, the gas stream comprises molecular oxygen, preferably from 0.1 to 10% and more preferably from 0.2 to 5%. Alternatively, the gas stream can comprise at least 0.04% of molecular oxygen. According to another preferred embodiment of the invention, the gas stream comprises molecular oxygen and a component selected from the group consisting of nitrogen, neon, argon, krypton, xenon, helium, oxygen, carbon monoxide, carbon dioxide, $N_2O$, gases of formula $NO_x$ wherein x represents 1, 2 or 3, air, and mixtures thereof. According to another preferred embodiment of the invention, the gas stream comprises nitrogen, argon and helium, in addition to molecular oxygen. Alternatively, it can comprise nitrogen, argon and nitrogen dioxide, in addition to molecular oxygen. The control of flow rate and/or gas pressure in the chamber, so as to obtain a Ultra Violet (UV) radiation of maximum intensity, can be carried out by selecting preferred ranges of values for at least one of these two parameters (flow rate and gas pressure). As an example, it can be done by selecting at least 2 or 3 (preferably at least 4) predetermined or constant values of flow rate and then measuring the UV emission intensity for each of these predetermined or constant values of flow rate as a function of pressure so as to select the parameters that permit to maximize the UV radiation intensity. Alternatively, it can also be done by selecting at least 2 or 3 (preferably at least 4) predetermined or constant values of pressure and then measuring the UV emission intensity for each of these predetermined or constant values of pressure as a function of the flow rate so as to select the parameters that permit to maximize the UV radiation intensity.

In preferred embodiments of the processes according to the first, second and third aspects, the gas stream can have one of the following compositions:

from 0.04 to 30% $O_2$; from 0.05 to 99.91% nitrogen; and from 0.05 to 99.91% argon;

from 0.04 to 30% $O_2$; from 0.05 to 99.91% nitrogen; and from 0.05 to 99.91% krypton;

from 0.04 to 99.90% $O_2$; from 0.05 to 99.91% nitrogen; and from 0.05 to 99.91% xenon or from 0.05 to 99.91% neon; or from 0.04 to 98.5% $O_2$; from 0.05 to 99.6% nitrogen; and from 0.05 to 99.6% xenon or from 0.05 to 99.6% neon.

Alternatively, the gas stream may consist of $NO_2$, nitrogen, or a mixture of oxygen and nitrogen and the pressure that is generated inside the sterilization chamber is then advantageously between 2 and 8 torrs.

In the processes of the first, second and third aspects of the invention the gas stream can alternatively consists of helium, neon, argon, krypton, xenon, or mixtures thereof. Preferably, the gas stream consists of argon.

In the processes of the first, second and fourth aspects of the invention, the ratio ratio R=(CDT)/(CSC) can be comprised between 0.01 and 0.70. CDT represents the cross-section of the discharge tube or the sum of the cross-sections of the discharge tubes and CSC represents the cross-section of the sterilization chamber. Preferably, $0.09 \leq R \leq 0.60$, more preferably $0.15 \leq R \leq 0.5$, even more preferably $0.2 \leq R \leq 0.40$. Alternatively, R can have a value between 0.05 and 0.20.

In the process according to the third aspect of the invention, wherein the sterilization chamber can be perpendicular to the direction of the gas stream feeding the discharge tube and cross-section (CSC) representing the cross-section of the chamber in communication with the discharge tube and which is perpendicular to the plasma current. Preferably, $0.09 \leq R \leq 0.60$, more preferably $0.15 \leq R \leq 0.5$, even more preferably $0.2 \leq R \leq 0.40$. In the sterilization device of the present invention, the electric field applicator can be of the surfatron or surfaguide type. The sterilization chamber can be entirely or partially made of borosilicate or aluminum. The sterilization chamber preferably comprises a support for the objects to be sterilized. The sterilization chamber is preferably cylindrical or parallelepipedal, and advantageously this sterilization chamber has a substantially constant cross-section.

According to another aspect of the present invention there is provided a process for sterilizing a contaminated object comprising exposing the object in a sterilization chamber to a plasma that is produced in at least one discharge tube that reaches the chamber, from a gas stream containing at least one gas of the group consisting of oxygen and rare gases such as helium, neon, argon, krypton and xenon. The sterilization chamber contains at least one discharge tube that reaches the chamber.

BRIEF DESCRIPTION OF DRAWINGS

Further features and advantages of the invention will become more readily apparent from the following description of preferred embodiments as illustrated by way of examples in the appended drawings wherein:

FIG. 13 illustrates the number of spore B. subtilis survivors as a function of time in a process for sterilizing a contaminated object according to another preferred embodiment of the invention, wherein a post-discharge of argon is used to sterilize the contaminated object.

DESCRIPTION OF PREFERRED
EMBODIMENTS

The following non-limiting preferred embodiments further illustrate the invention.

Figure 1:
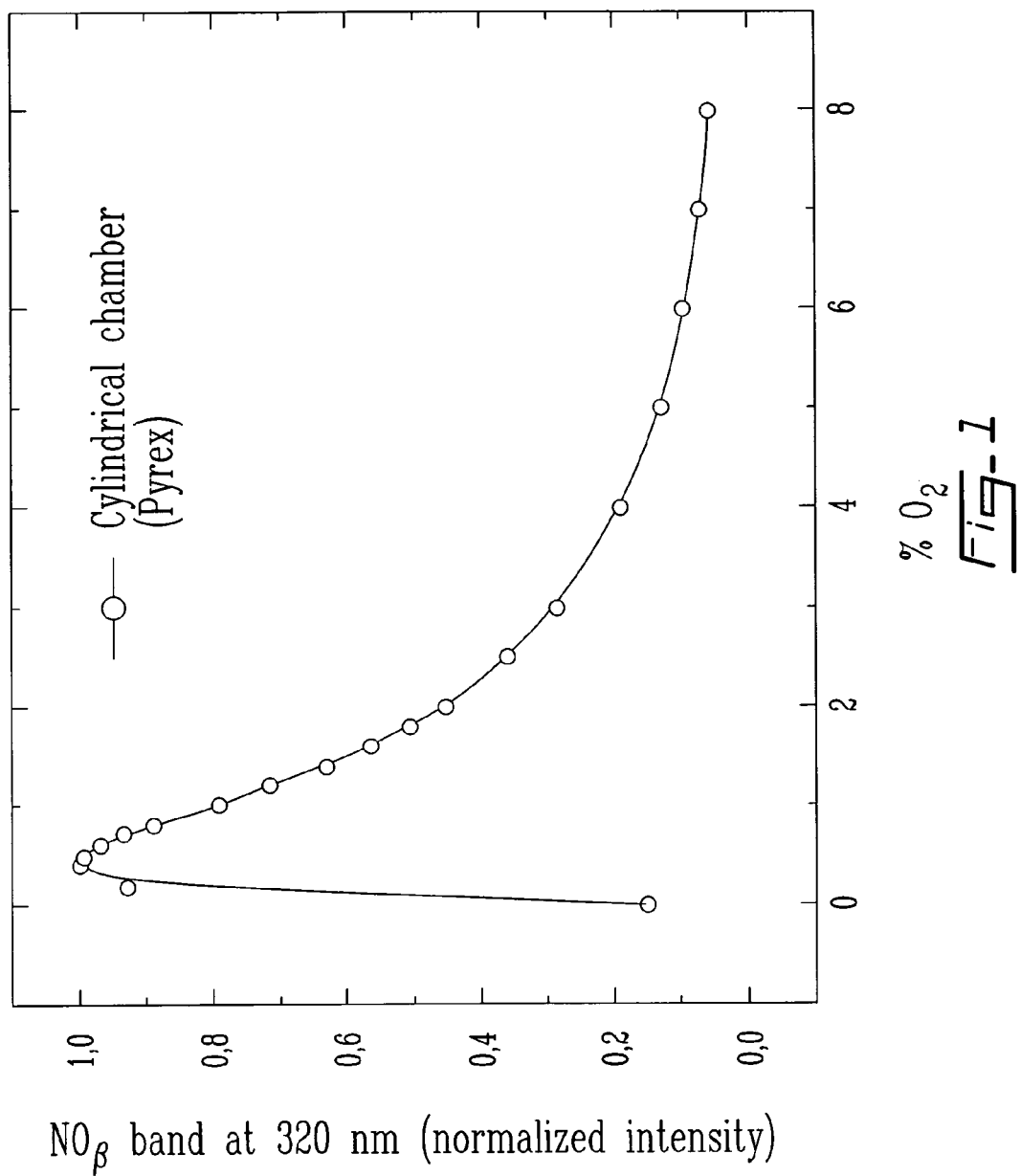
FIG. 1 illustrates the relative intensity variation of UV photon emission as a function of the percentage of $O_2$ in a $N_2/O_2$ mixture, in a process for sterilizing a contaminated object according to a preferred embodiment of the invention.
Figure 5:
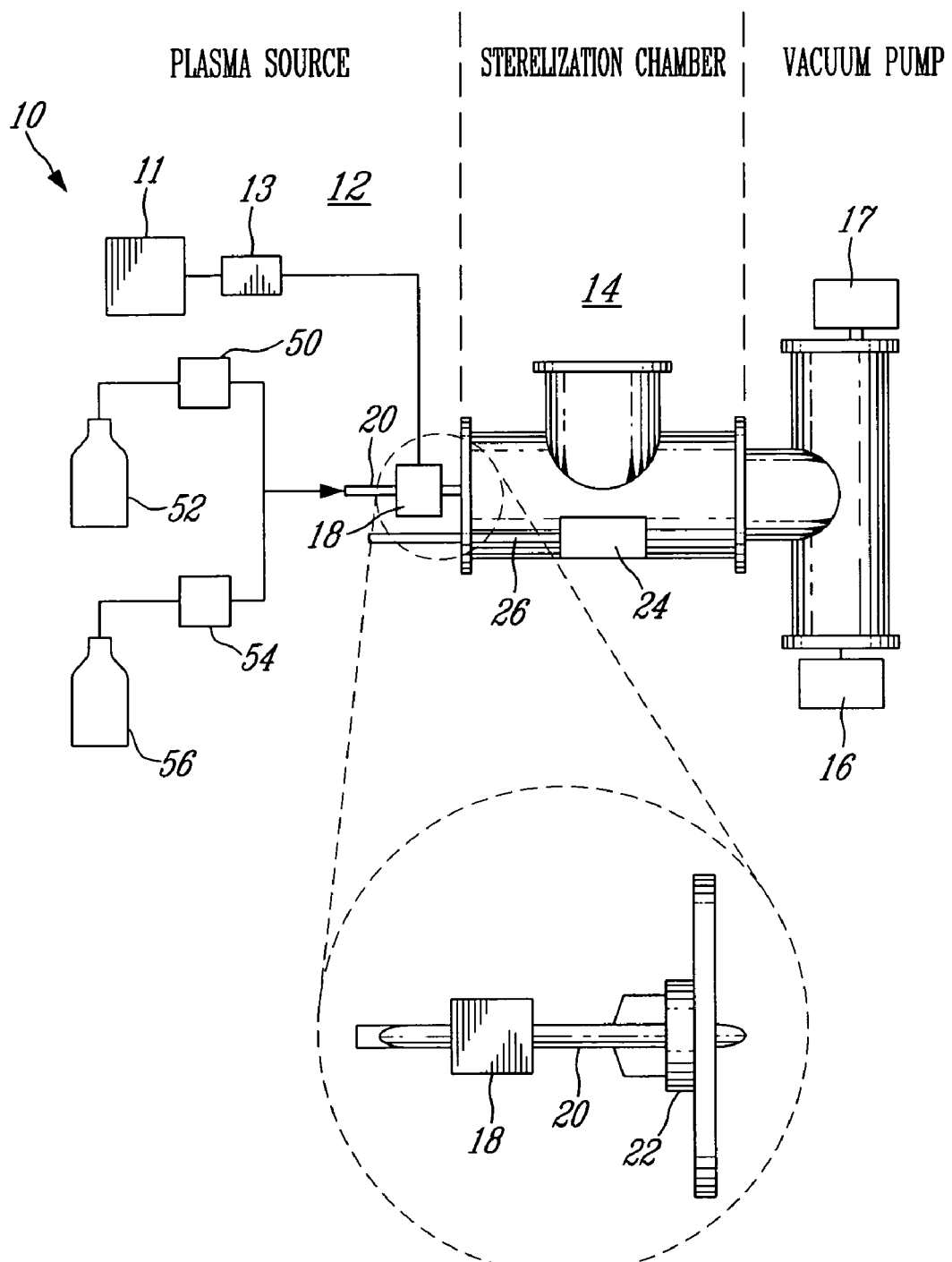
FIG. 5 illustrates a sterilization device as described in U.S. Pat. No. 6,707,254, which is hereby incorporated by reference.

FIG. 1 represents the intensity variation of UV photon emission, measured at 320 nm in the $NO_\beta$ (250-380 nm) band, as a function of the percentage of $O_2$ added to $N_2$ in the $N_2/O_2$ mixture that feeds the discharge tube of a cylindrical sterilization chamber. This experiment has been carried out by using according a device having 20 L sterilization chamber as illustrated in FIG. 5. Such a device is provided with a discharge tube whose inner diameter is 6 mm, and a high frequency generator that emits a wave at the 2450 MHz frequency at an output power of 100 W. The chamber was operating at a pressure of 5 torrs and a flow rate of 1 liter standard/minute (slm).

Figure 2:
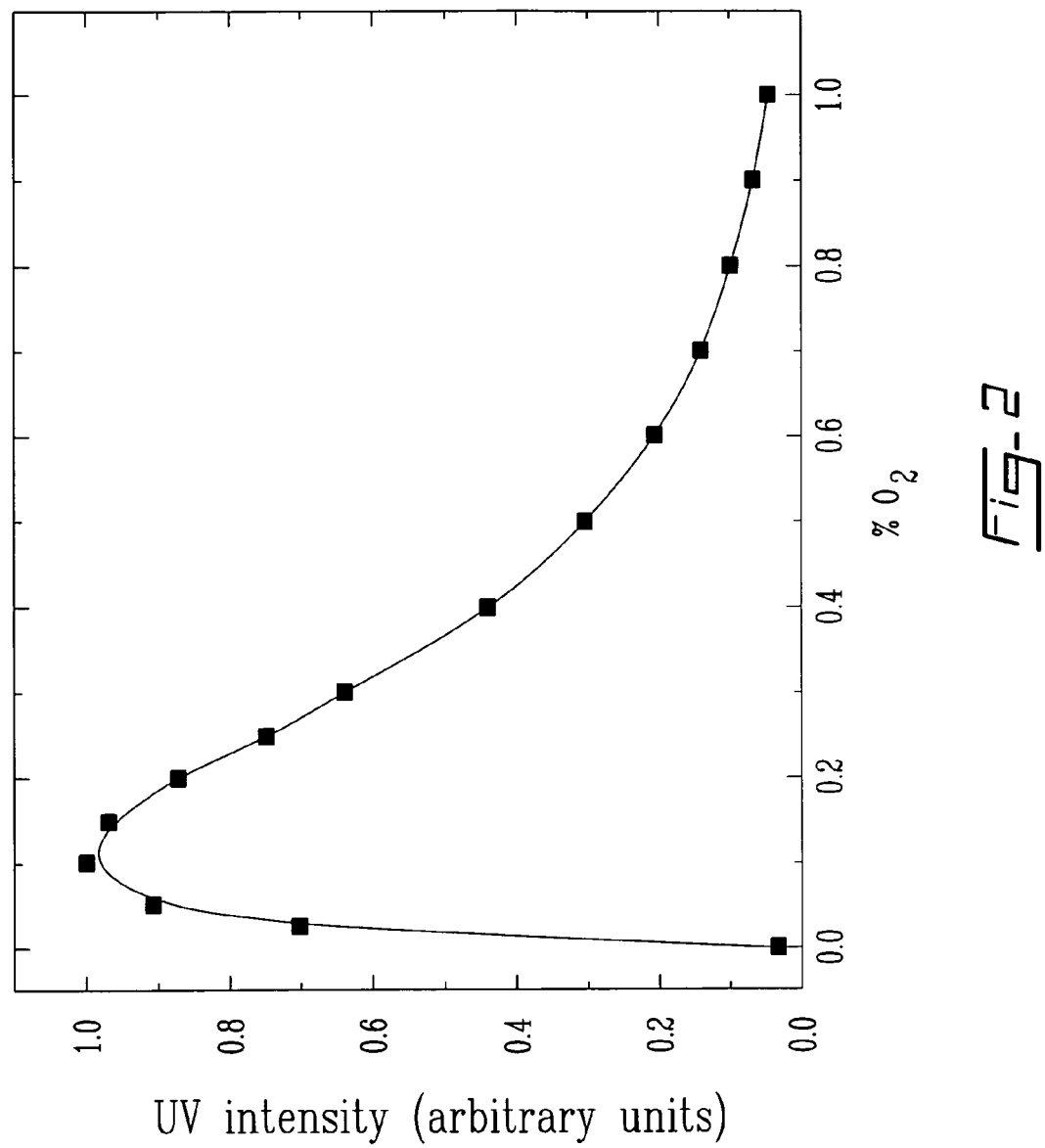
FIG. 2 illustrates the relative intensity variation of UV photon emission as a function of the percentage of $O_2$ in a $N_2/O_2$ mixture, in a process for sterilizing a contaminated object according to another preferred embodiment of the invention.

In FIG. 2, the intensity variation of UV photon emission, measured at 320 nm in the $NO_\beta$ (250-380 nm) band as a function of the percentage of $O_2$ added to $N_2$ in the $N_2/O_2$ mixture is shown. This experiment was carried out by using a parallelepipedal sterilization chamber of 50 Liters similar to the device illustrated in FIG. 6. The discharge tube had an inner diameter of 26 mm. A high frequency generator that emits a wave at the 915 MHz frequency at an output power of 300 W was used. The chamber was operated at a pressure of 6 torrs, with a flow rate of 1 slm.

Figure 3:
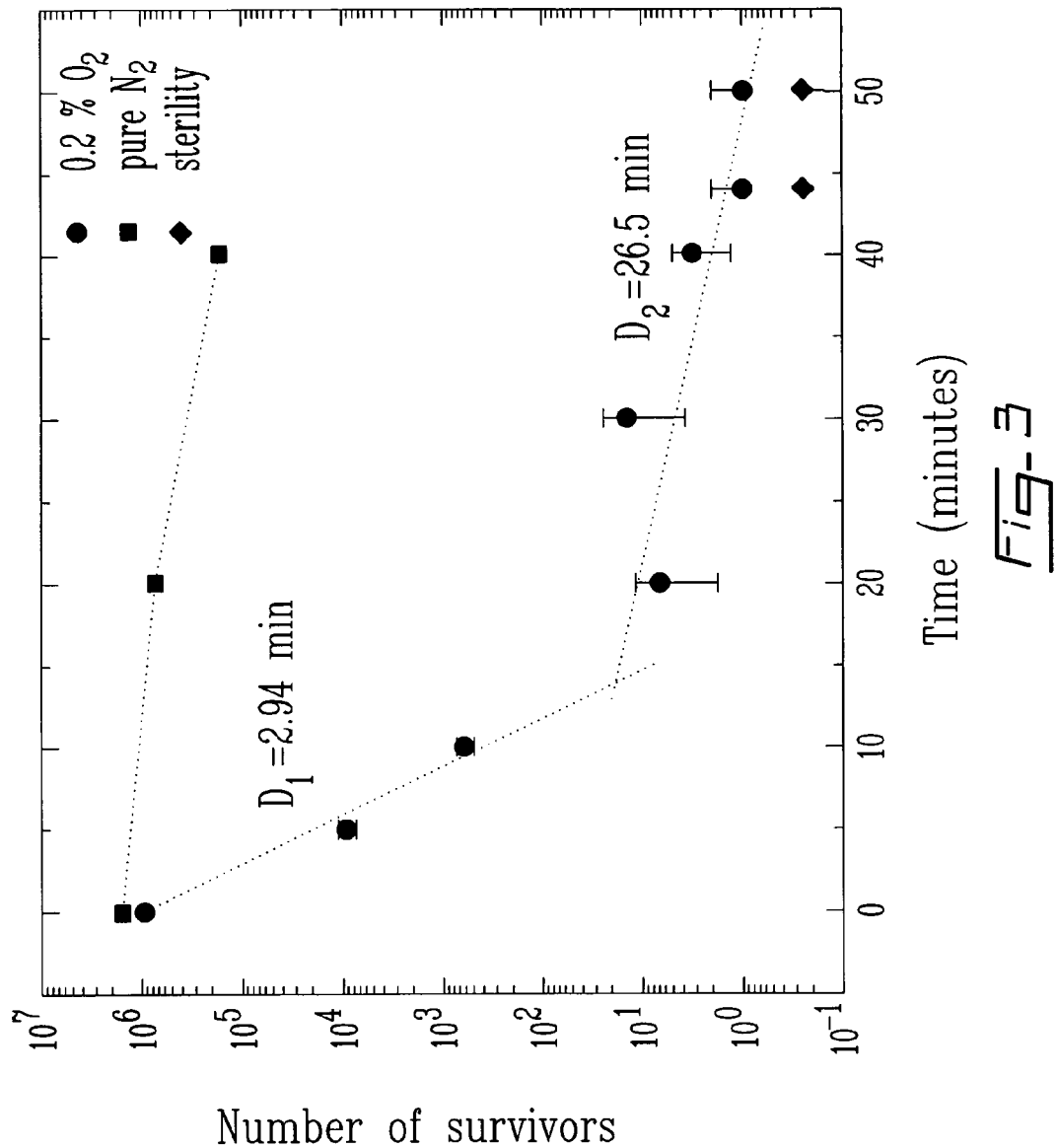
FIG. 3 illustrates the number of spore B. subtilis survivors as a function of time in a process for sterilizing a contaminated object according to another preferred embodiment of the invention, wherein a post-discharge of a $N_2/O_2$ mixture is used to sterilize the contaminated object.
Figure 6:
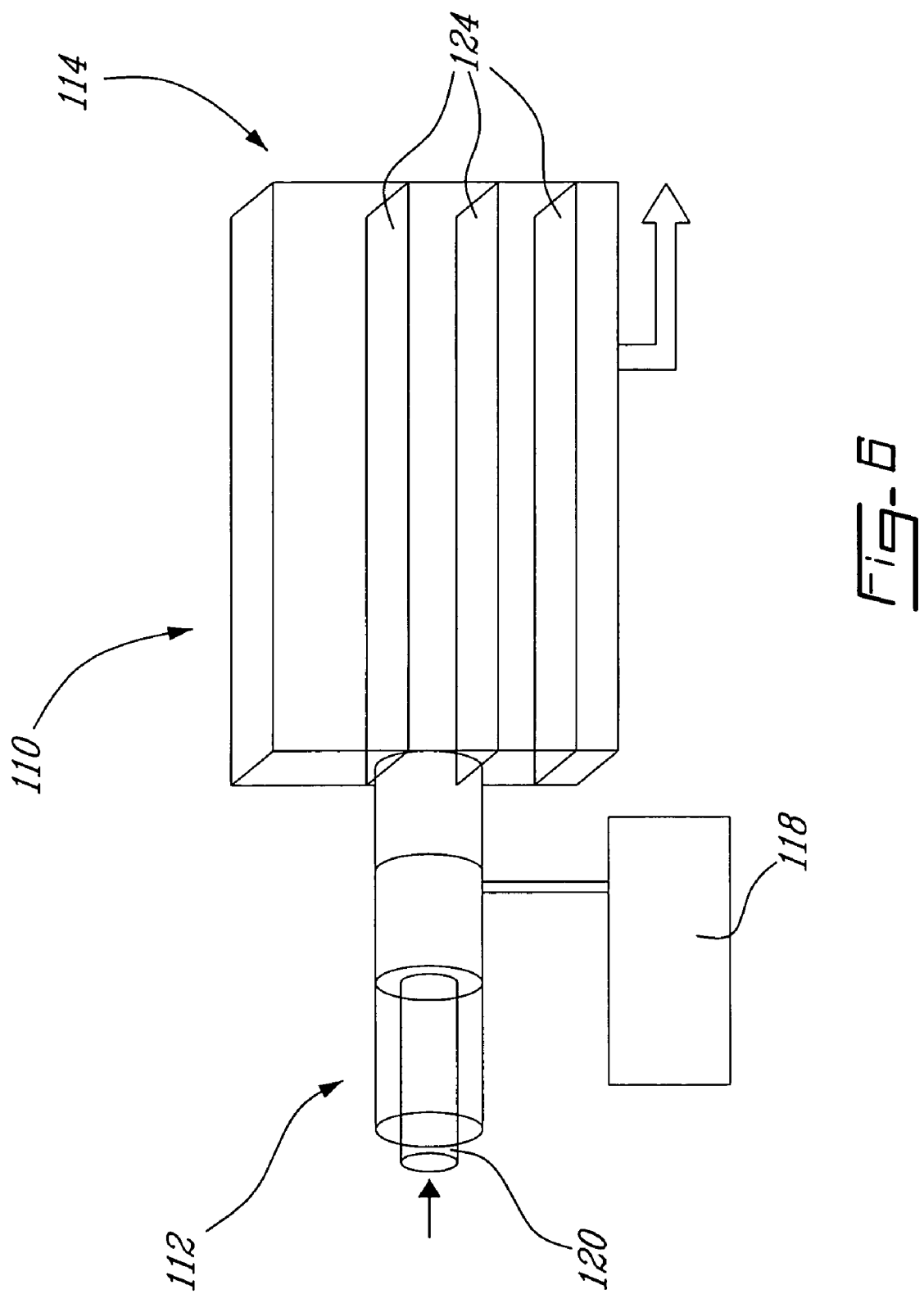
FIG. 6 illustrates a sterilization device according to another preferred embodiment of the invention.

As it can be seen in FIG. 3, the number of survivors will considerably vary as a function of the $O_2$ percentage in the $N_2/O_2$ mixture. FIG. 3 represents a diagram of spore *B. subtilis* survivors that have been exposed to a post-discharge of $N_2/O_2$ at 0 and 0.2% of $O_2$. Sterilization was obtained in a chamber as illustrated in FIG. 6 in about 40 minutes, with 0.2% $O_2$. Sterility has been checked according to the method of positive tests (lozenge symbol). Time D indicated for each phase represents the time required to reduce spore population by 90%. The chamber was operated at a pressure of 8 torrs, with a flow rate of 2 slm, and at an output power of 300 W. It thus appears that at least a minimum of oxygen was required in order to have a reasonable time of sterilization.

Figure 4:
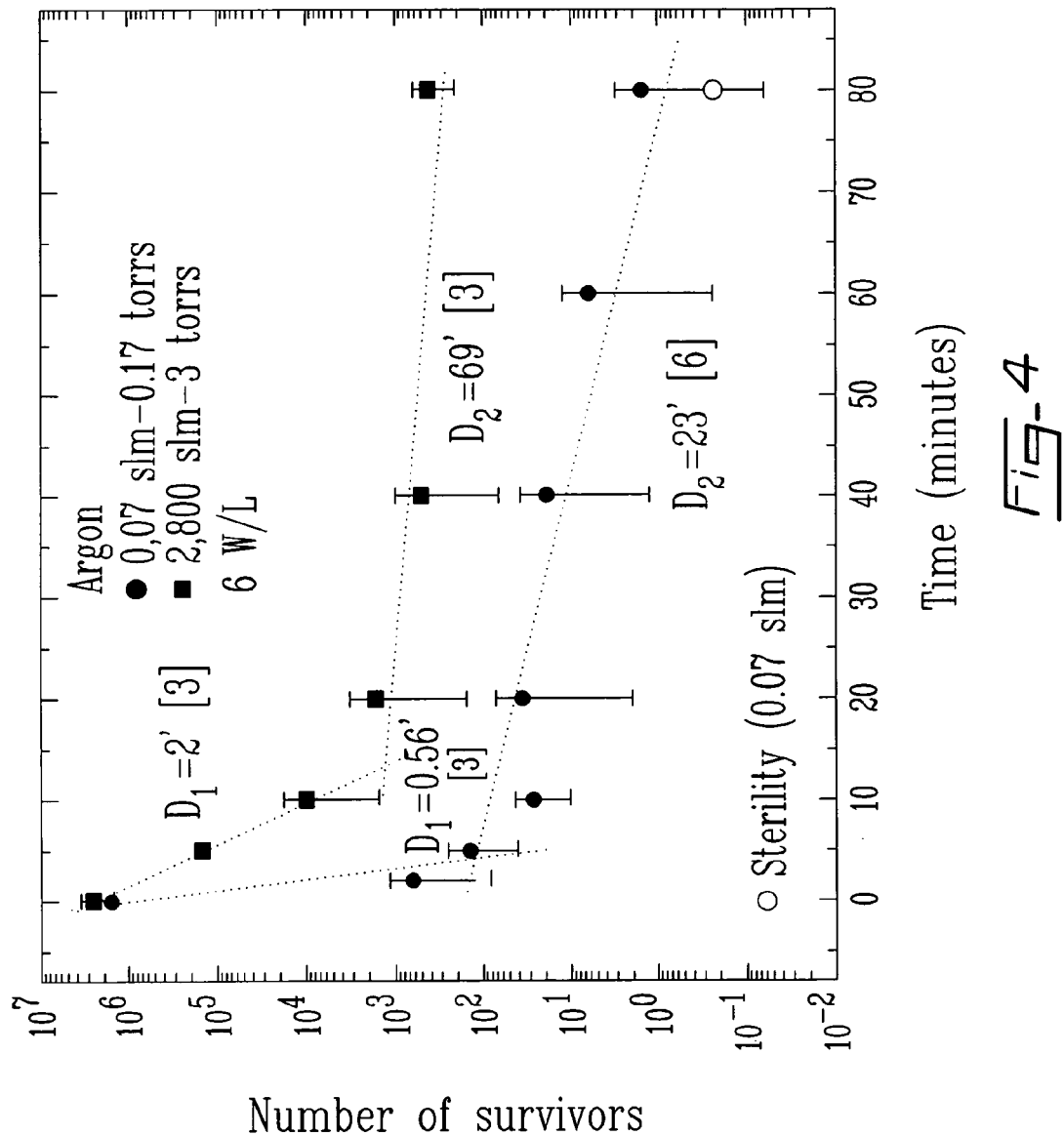
FIG. 4 illustrates the number of spore B. subtilis survivors as a function of time in a process for sterilizing a contaminated object according to another preferred embodiment of the invention, wherein a post-discharge of argon is used to sterilize the contaminated object.

However, as shown in FIG. 4, Applicants have obtained surprising and very interesting results by using a gas stream consisting of argon. These results are quite surprising in view of FIG. 3 were it has been shown that the presence of $O_2$ seemed to be required. Moreover, in U.S. Pat. No. 6,707,254 the use of a discharge consisting of argon alone did not lead to sterilization in a reasonable time, as shown in FIGS. 4 and 6 of this prior art document. These results in U.S. Pat. No. 6,707,254 have been obtained at a working pressure between 3.2 and 7 torrs at a flow rate of 2 slm. As it can be seen from FIG. 4 of the present application, sterility was obtained quite rapidly (80 minutes) in a chamber similar to the chamber illustrated in FIG. 6 by using an argon gas stream, provided that the experiment was carried out with the right combination of gas pressure and flow rate, namely at 0.07 slm and 0.17 torrs. At 3 torrs., sterility is not obtained at 2.8 slm since there are still more than 500 spores to be inactivated after 80 minutes.

FIG. 5 shows the device as described in U.S. Pat. No. 6,707,254. This device 10 for sterilization comprises a plasma source 12, a $N_2$ mass flow controller 50, a $N_2$ source 52, an $O_2$ mass flow controller 54, an $O_2$ source 56, a post-discharge chamber as the sterilization chamber 14, a vacuum pump 16, and a pressure indicator 17 which controls the gas pressure. The plasma is produced by a microwave discharge at 2.45 GHz by propagation of an electromagnetic surface wave at a maximal power of 180 W from a generator 11. The power is measured from a power meter 13. For a power of about 100 W or more, it is preferable, particularly if the object to be sterilized is thermally sensitive, to cool the discharge tube 20 with compressed air. The surface wave is excited by a conventional surfatron 18. Any other device for exciting the surface wave, such as those described in U.S. Pat. Nos. 4,043,940; 4,810,933, or in J. Phys. D.: Appl. Phys. 1991, 24, 1025-1048 may be used, which allows the broadening of the range of possible frequencies from a few MHz to some GHz. The diameter of the discharge tube 20 through which the plasma is injected in chamber 14 is not critical, but is preferably chosen in order to optimize the production of requested species for the sterilization. According to the embodiment illustrated in FIG. 5, the internal diameter of the tube is of 8 mm and its length is 300 mm. The discharge tube may be fabricated with any material compatible with the operation of the system, for example from fused silica.

In order to prevent overheating of vacuum sealing elements (o-rings) placed between chamber 14 and tube 20, which is generated by the microwaves and the plasma, the diameter of tube 20 is expanded to 30 mm at extremity 22 which is adjacent to chamber 14. The gas(es) is (are) introduced into tube 20 at a rate which is adjusted with the help of a flowmeter (for example, 50 and/or 54) which is previously calibrated. The gases are conducted into chamber 14 by means of pump 16 generating a primary vacuum (residual vacuum of 30 to 50 mtorr). A more or less important throttling of the pump allows the gas pressure to be fixed in the reactor. Evacuation of the gas from pump 16 is done outside the building, eventually through appropriate filters. The pressure inside the chamber is preferably reduced at a value situated between 30 and 50 mtorr, and the pressure of the gas entering the chamber is adjusted preferably between 1 and 7 torr.

Chamber 14 has a volume of 20 liters, and is made of Pyrex™ (i.e., borosilicate glass), but can be made of any material compatible with the reaction mixture. Pyrex™, due to its transparency, is particularly advantageous since it allows observations by emission spectroscopy, to see the effects of the positioning of the object to be sterilized on the gaseous flux, etc. Advantageously, the objects to be sterilized are placed in a support 24 that is preferably made of stainless steel. The form of the support is suited to facilitate its cleaning after use, as well as the retrieval of the sterilized objects. In order to set the temperature in the support 24, it is possible to circulate in it, in a closed circuit, a cooling liquid inside a duct 26, also made of stainless steel.

FIG. 6 illustrates a sterilization device 110 according to the present invention. The device has a source of plasma 112, a sterilization chamber 114 of parallelepidal shape, and a discharge tube 120. The chamber 114 is made of aluminum. Preferably, the chamber 114 is provided with observation windows (not shown) so as to carry out optical spectroscopy measurements. The device 110 also comprises a generator 118 and supports 124 for receiving the objects to be treated. The chamber has a capacity of 50 liters (known conventional sterilizers have a capacity of 50, 100 or 150 liters). The device 110 also comprises several of the same elements as defined in FIG. 5 (such as pump, cooling duct, pressure gauge, surfatron, power meter etc. (not shown)) and is operated in a similar manner. Uniformity of the active species in the sterilization chamber, which ensures that the objects are sterilized notwithstanding their position in the chamber, and which minimizes high gas flow turbulence effects (it is then possible to operate at 2-3 slm without turbulence), has been obtained thanks to a tube whose widened discharge diameter is 26 mm (to achieve this, microwave frequency was also decreased from 2450 MHz to 915 MHz (R=0.09). Indeed, the device of FIG. 5 (R=0.04) was truly efficient only in the vicinity of the axis of the discharge tube.

Figure 7:
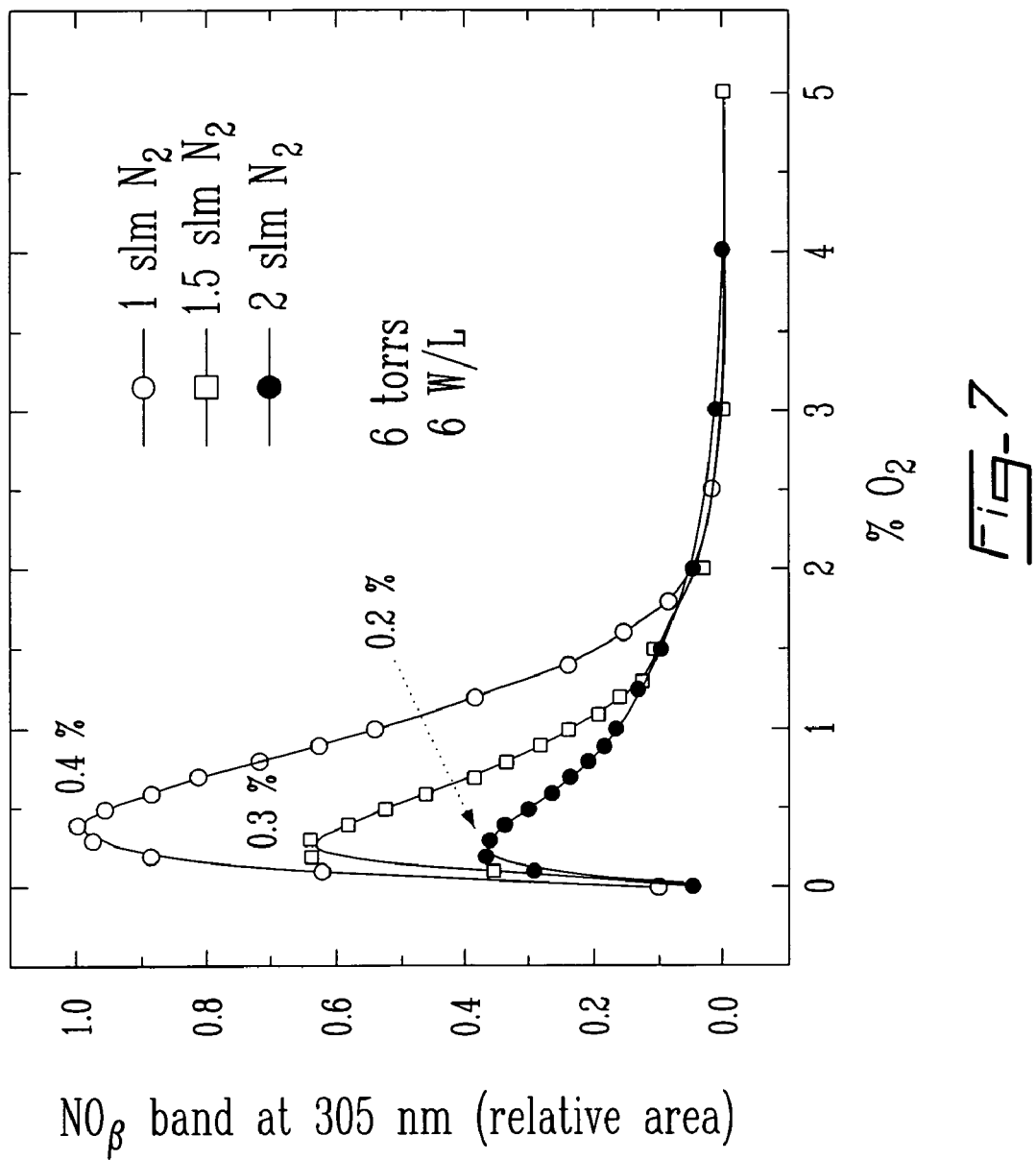
FIG. 7 illustrates the relative variation of the UV emission intensity as a function of the percentage of molecular oxygen present in a $N_2/O_2$ mixture, at different flow rates, in a process for sterilizing a contaminated object according to another preferred embodiment of the invention.

FIG. 7 shows the relative variation of the UV emission intensity as a function of the percentage of $O_2$ in a $N_2/O_2$ mixture at different flow rates. The optimum percentage of oxygen, given the gas flow rate, is indicated on each curve. Intensity of the UV signal is collected at the inlet of the chamber of a device similar to the device of FIG. 6.

Figure 8:
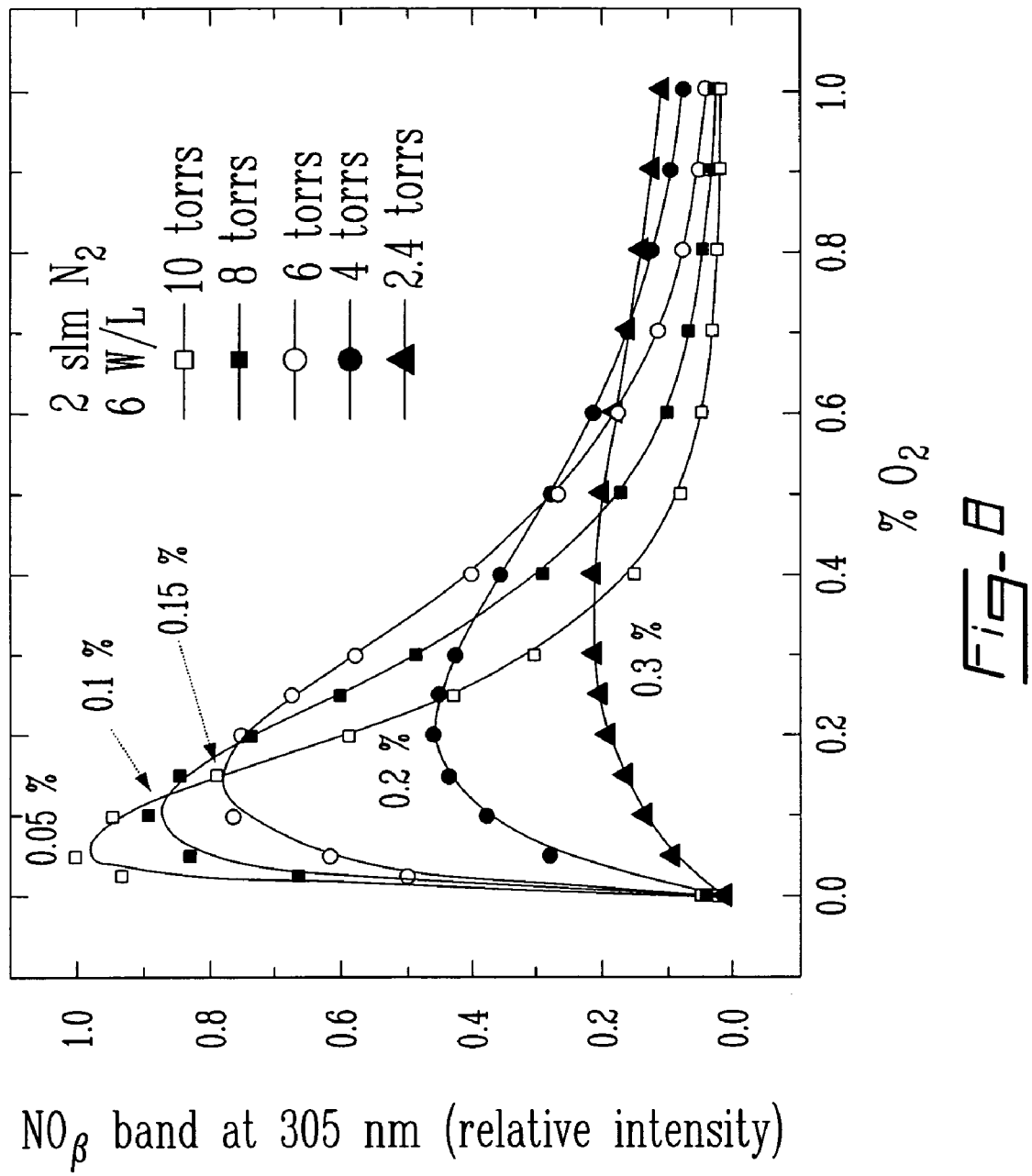
FIG. 8 illustrates the relative variation of the UV emission intensity as a function of the percentage of molecular oxygen present in a $N_2/O_2$ mixture, at different pressures, in a process for sterilizing a contaminated object according to another preferred embodiment of the invention.

FIG. 8 shows the relative variation of the UV emission intensity as a function of the percentage of $O_2$ in a $N_2/O_2$ mixture at different pressures and for a fixed flow rate, in a sterilization chamber similar to the one illustrated in FIG. 6.

It can thus be seen from FIGS. 7 and 8 that by adjusting the flow rate and the pressure at optimum values, the intensity of Ultra Violet (UV) radiation can be maximized.

Figures 9A, 9B:
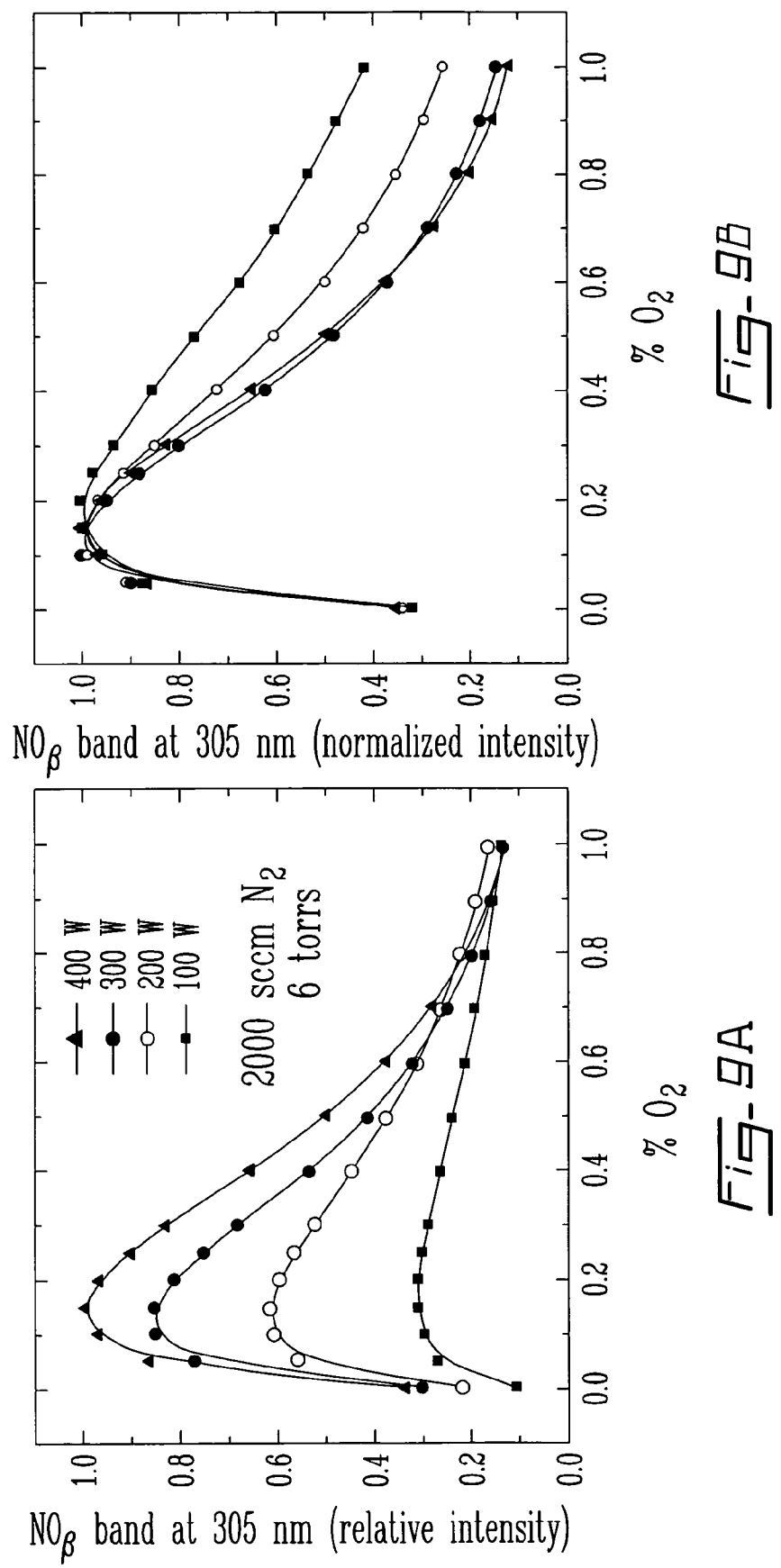
FIG. 9A illustrates the relative variation of the UV emission intensity as a function of the percentage of molecular oxygen present in a $N_2/O_2$ mixture, at different microwave power intensities, in a process for sterilizing a contaminated object according to another preferred embodiment of the invention.
FIG. 9B illustrates the relative variation of the UV emission intensity as a function of the percentage of molecular oxygen present in a $N_2/O_2$ mixture, at same or normalized microwave power intensities, in a process for sterilizing a contaminated object according to another preferred embodiment of the invention.

FIGS. 9A and 9B show the influence, in a sterilization chamber similar to the chamber of FIG. 6, of microwave power on UV emission intensity variation as a function of the percentage of $O_2$ in a mixture $N_2/O_2$. In FIG. 9A, the UV emission is expressed in relative intensity and in FIG. 9B the UV emission intensity is further expressed normalized to unity.

Figure 10:
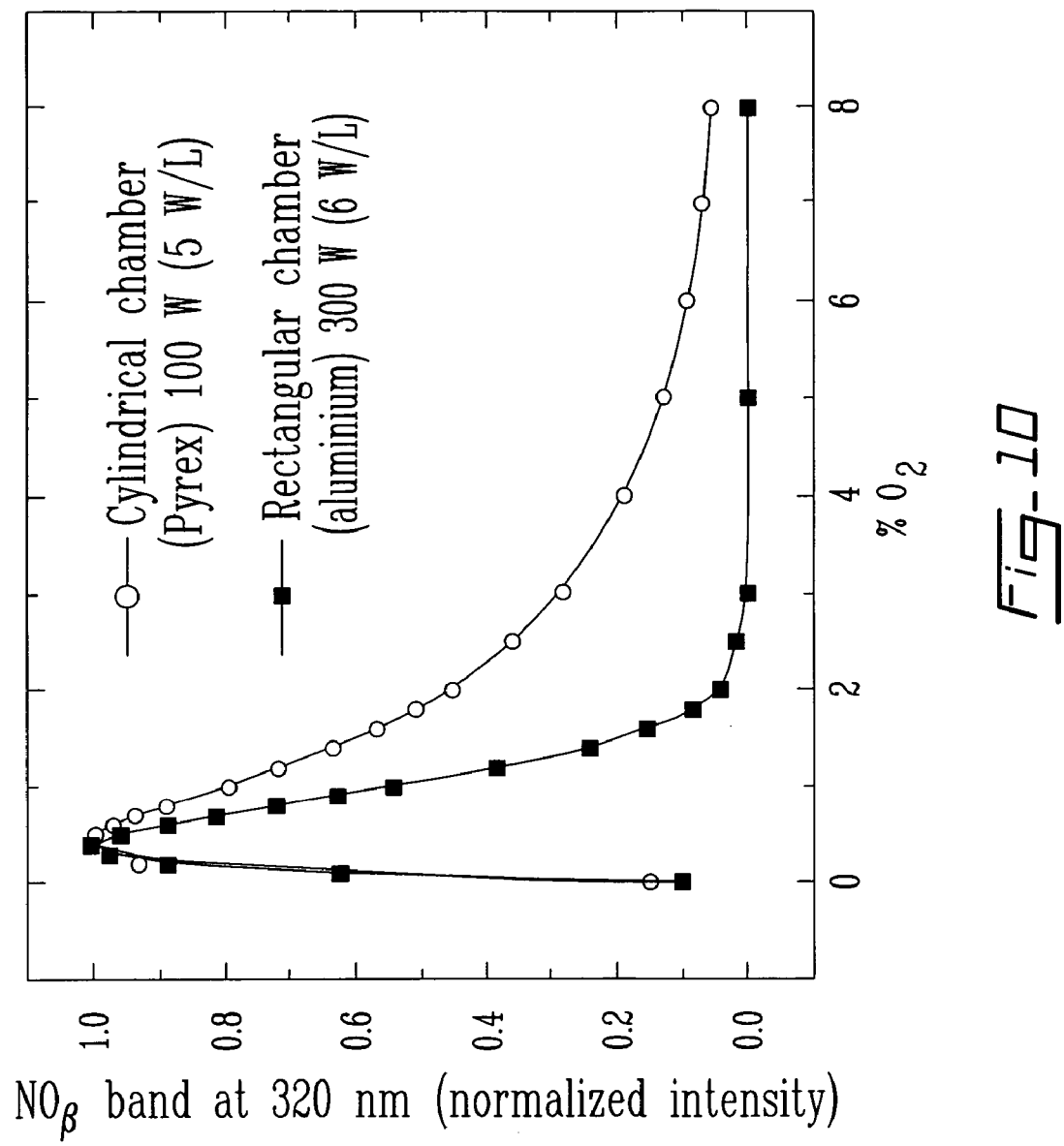
FIG. 10 illustrates the relative variation of the UV emission intensity as a function of the percentage of molecular oxygen present in a $N_2/O_2$ mixture, in different sterilization chambers, during a process for sterilizing a contaminated object according to another preferred embodiment of the invention.

In FIG. 10 a comparison between two different chambers under similar conditions (1 slm of $N_2$, pressure 5 torrs) is represented. The relative variation of the UV emission intensity is expressed as a function of the percentage of $O_2$ in a $N_2/O_2$ mixture. In the 20 L cylindrical chamber similar to the chamber of FIG. 5, power is 100 W, i.e., 5 W/L, while in the 50 L parallelepipedal chamber power is 300 W, i.e., 6 W/L. Intensities are normalized to unity.

Figure 11:
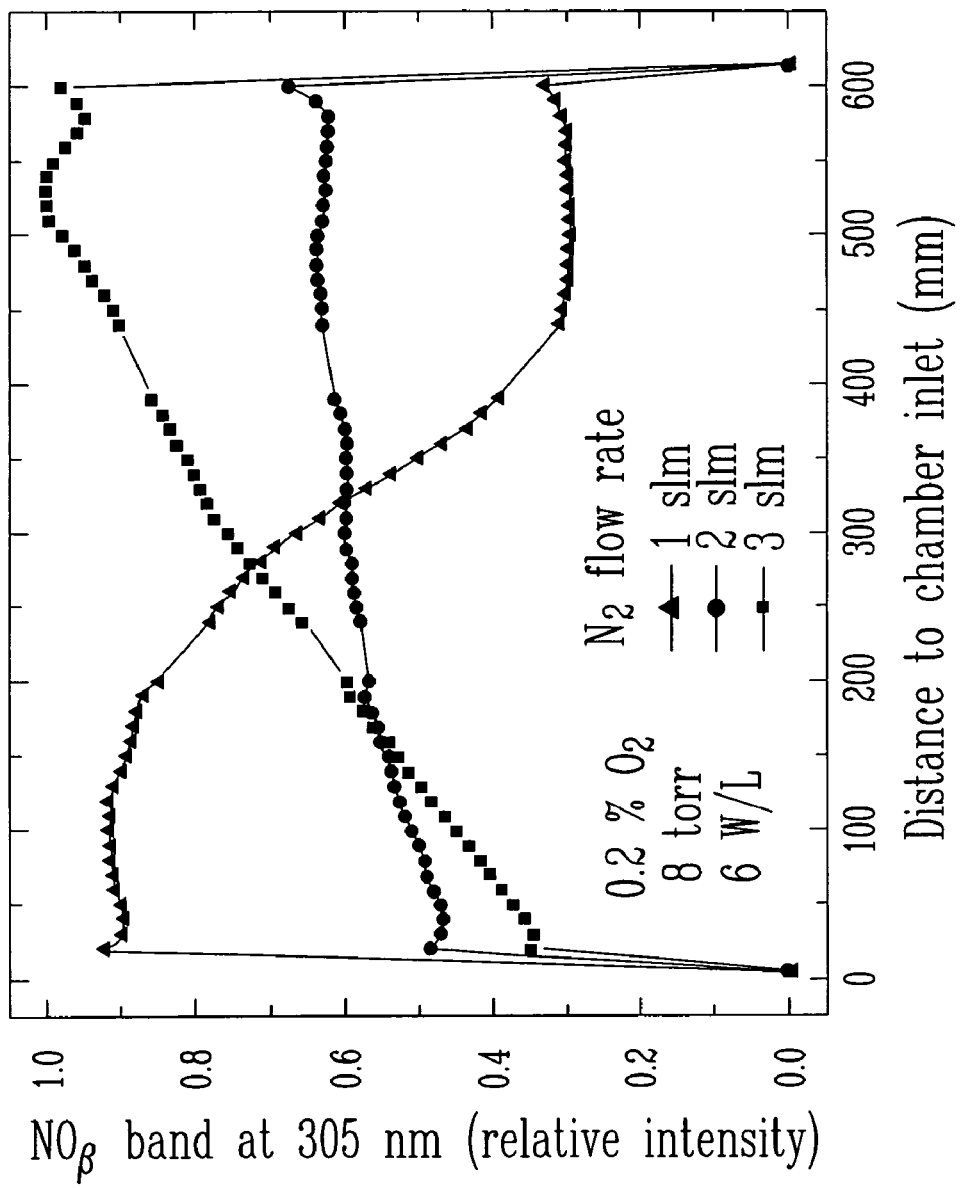
FIG. 11 illustrates the UV emission intensity relative variation along the discharge axis, for different $N_2$ flow rates with a fixed percentage of $O_2$ and at constant pressure, in a process for sterilizing a contaminated object according to another preferred embodiment of the invention, wherein a $N_2/O_2$ mixture is used for sterilizing the contaminated object.

In FIG. 11, the results presented refer to the uniformity obtained in the sterilization chamber along the discharge tube axis during the treatment. The UV emission intensity is plotted at different nitrogen flow rates, with a fixed percentage of added oxygen (0.2%) in the $N_2/O_2$ mixture and at a constant pressure of 8 torrs. At about 2 slm, the observed UV intensity is relatively uniform along the chamber. The chamber used is similar to the chamber of FIG. 6.

Figure 12:
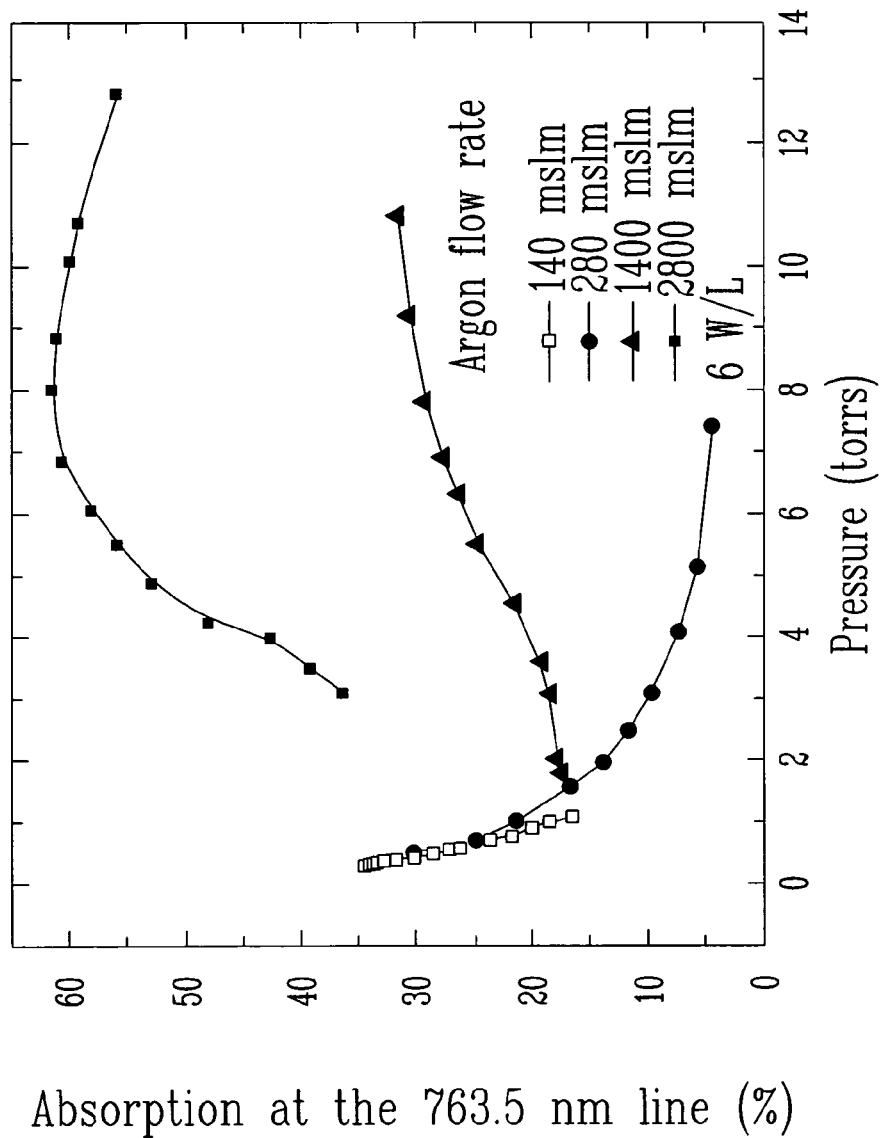
FIG. 12 illustrates that in a process for sterilizing a contaminated object according to another preferred embodiment of the invention, maximum UV intensity at a given pressure is observed to depend on the flow rate of gas.

In FIG. 12, several tests have been made with gas streams consisting of argon. In fact, various flow rates have been tested so as to check the influence on the UV emission intensity. It has thus been demonstrated that the pressure at which maximum UV intensity is observed, depends a lot on the flow rate of argon. If the flow rate is weak (□), the operating pressure should be low. On the contrary, if the flow rate is high (■), the optimum pressure should be high.

In fact, as shown in FIG. 12, an improvement of the sterilization treatment can be carried by obtaining by maximizing the Ultra Violet (UV) radiation intensity. By measuring the UV emission intensity for a given flow rate (constant flow rate) as a function of pressure, a preferred range of values of pressure is thus obtained for such a given flow rate. Such a measurement is also preferably done for at least 2 or 3 other given values of flow rate (as example see the flow rates of 140, 280, 1400, and 2800 mslm in FIG. 12) in separate experiments. Thus, such experiments permit to select parameters that allow to maximize the UV radiation intensity, thereby optimizing the sterilization treatment by eventually reducing the time required for obtaining sterility of the treated object (see FIGS. 3, 4, and 13). The person skilled in the art will also understand that alternatively, such an optimization of the process can be done by measuring the UV emission intensity for a given pressure (constant pressure) as a function of the flow rate. Thus, a preferred range of values of flow rate is thus obtained for such a given pressure. Such a measurement is also preferably done for at least 2 or 3 other given values of pressure in separate experiments.

FIG. 13 shows a spore *B. subtilis* survival curve in a post-discharge consisting of argon, in a sterilization chamber chamber similar to the chamber of FIG. 6, In FIG. 13, given the pressure of 0.1 torrs, the gas flow was carefully adjusted to yield a UV emission intensity close to maximum. FIG. 13, compared to FIG. 4, shows that optimizing UV intensity reduces sterilization time: sterility is attained in FIG. 13 in 40 minutes while it required 80 minutes in FIG. 4 (0.07 slm, 0.17 torrs).

The following non-limiting examples further illustrate the invention.

EXAMPLES

Description of a Commercial Form of Plasma Sterilizing Device

The present device is presented by way of illustration only and should not be interpreted as constituting any kind of limitation to the object of the present invention. It comprises three main elements: a plasma source, a sterilization chamber where the objects to be sterilized are disposed (for example, on grids (acting as support)), and a vacuum pump to: 1) initially evacuate the chamber to a residual pressure of about 20-50 mtorr, and 2) thereafter maintain the desired pressure in the presence of the gas flow rate while simultaneously making sure that the active species are renewed by continuous evacuation of the gases. The tested sterilization chambers were built of aluminum, which is a light and inexpensive material. They may by cylindrical or parallelepipedal. Means for supporting objects (such as a grid) to be sterilized are integrated in the chamber, and the latter is advantageously provided with an access door allowing to load and unload the sterilizer.

The sources of plasma: 1) allow a sufficient UV radiation to achieve sterilization in at most 40 minutes; 2) make sure that the active species in the chamber are uniform. To this end, the diameter of the discharge tube with respect to the cross-section of the chamber (diameter that determines the upper working frequency) is kept as large as possible, but actually not too large to make the device cumbersome or costly. More than one source of plasma may be used, the latter being adequately disposed, and the gas stream is adjusted to optimize this uniformity; 3) make sure that the temperature does not exceed 50 to 60° C. in the chamber; and 4) utilize gases and operating conditions that minimize damages caused to the objects by this sterilizing process (in particular, utilizing as little $O_2$ as possible in the gas mixtures or avoid use of $O_2$).

The sterilizing system comprises a device ensuring the sterilization cycle: evacuation of the chamber, gas delivery, pressure and flow rate control, supplying microwave output and ignition of discharge; at the end of the cycle, return to atmospheric pressure. To control the good operation of the sterilizer, the physical parameters are checked (base vacuum, pressure and gas flow rate, incident and reflected microwave powers, UV radiation intensity in the chamber in at least two points and recording of this intensity all during the plasma cycle). Finally, at the end of the cycle, the treatment parameters with traceability of the sterilized objects are printed.

The results which follow have been obtained in a parallelepipedal sterilization chamber (50 liters), except in FIGS. 1, 5, and 10 (in part).

Determination of the Uniformity of Distribution of UV Radiation in the Sterilization Chamber is Carried Out in the Examples in the Following Manner.

The sterilization chamber FIG. 6 is provided in the present case with a fused silica window, through which UV are transparent above 180 nm. Light emitted by a post-discharge volume element is collected, via a collimator, by an optic fiber that is connected to the input slit of the optical spectrometer. The optical spectrometer (using a diffraction grating) allows to record UV emission intensity of the post-discharge at a given wavelength. The collimator-optical fiber combination is designed so as to be movable in a plane according to the X and Y axes, thus making it possible to obtain a cartography, longitudinally and transversely, of the UV emission intensity (normally recorded at 320 nm).

Maximum UV Emission on the $NO_\beta$ Band as a Function of the Percentage Of $O_2$ in the $N_2/O_2$ Mixture.

The results obtained, unless indicated otherwise, in a device similar to the device shown in FIG. 6 including a single discharge tube and supplied with a gas mixture consisting of $N_2$ and $O_2$. Ratio R=0.09.

Variation of the Optimum Percentage of $O_2$ with Respect to Flow Rate

The results reported in FIG. 7 show the relative variation of the UV emission intensity as a function of the percentage of added oxygen, with different flow rates. On each curve, the optimum percentage of oxygen is specified. Signal intensity is collected at the inlet of the chamber. It is realized that the optimum percentage of molecular oxygen, for realistic gas streams, is between 0.1 and 0.4 $O_2$ added to $N_2$ to constitute the $N_2/O_2$ mixture.

Variation of the Optimal Percentage of $O_2$ with Respect to Pressure

The results reported in FIG. 8 show the relative variation of the UV emission intensity as a function of the percentage of oxygen added to $N_2$ under different pressures. For a flow rate of 2 slm, the optimal percentage is between 0.05% $O_2$ (10 torrs) and 0.3% (2.4 torrs) where the pressures under consideration are realistic.

Variation of the Optimal Percentage of $O_2$ with Microwave Power that is Absorbed in the Discharge and Reported to the Capacity of the Sterilization Chamber (1 to 8 W/liter)

The results reported in FIGS. 9(A and B) show the influence of microwave power used on the relative variation of the UV emission intensity as a function of the percentage of oxygen. (a) relative intensities; (b) same intensities, but normalized to unity It is realized from FIG. 9(B) that, for a given pressure and gas stream, the power that is dissipated in the discharge has only little influence on the relative variation of the UV emission intensity, although it affects its absolute value, as shown in FIG. 9(A).

Variation of the Optimal Percentage of $O_2$ with Respect to the Design and Capacity of the Chamber The two chambers, studied by way of comparison in the present example, are those represented in FIGS. 5 and 6. The results reported in FIG. 10 compares the relative variation of the UV emission intensity as a function of the percentage of molecular oxygen in the two chambers: 1 slm $N_2$—5 torrs; Pyrex chamber (5 W/L) vs parallelepipedal (6 W/L). Intensities are normalized. A study of the UV emission intensity variation profile as a function of the percentage of $O_2$ added to $N_2$ shows a maximum for the same percentage in the two chambers (independence of operating parameters, namely microwave frequency, diameter of the discharge tube, geometry and nature of the chamber, ratio R, position of the pumping orifice,); on the other hand, a decrease of UV intensity is carried out less rapidly in the cylindrical chamber. It should be noted that the cylindrical chamber FIG. 5 is fed with a discharge at 2450 MHz while the parallelepipedal chamber is fed with a 915 MHz discharge. Conclusion: in the examples shown, the optimal percentage is between 0.05 and 0.4% $O_2$ added to $N_2$ thus covering a wide range of variation of the operating parameters (microwave frequency, flow rate, discharge tube diameter,).

Improvement of Spatial Distribution Uniformity of UV Photon Emitting Species in the Sterilization Chamber The results which follow have been obtained in a device similar to the 50 liter parallelepipedal chamber schematically illustrated in FIG. 6. Measurements were carried out by optical emission spectroscopy at a wavelength (320 nm) which is representative of the $NO_\beta$ band emission intensity.

The results that are reported in FIG. 11 represent UV emission intensity variation along the axis of the discharge tube into the rectangular chamber, for different flow rates of nitrogen, with fixed percentage of added oxygen (0.2%) and under constant pressure. At about 2 slm, UV intensity is relatively uniform along the chamber.

For a given pressure (or in the immediate neighborhood) under optimum $O_2$ for UV emission intensity, a control of the flow rate of $N_2$ (here at 2 slm) makes it possible to obtain a uniform UV emission along the chamber (plasma discharge is located on the left of FIG. 11). If uniformity is intended at another flow rate, the pressure inside the chamber preferably has to be modified accordingly.

Inactivation of the Spores with a Post-Discharge of a Gas Stream of Pure Argon (or Consisting of Argon)

The results reported in FIG. 12 show absorption of the argon line at 763.5 nm as a function of pressure for different flow rates. Measurements were made at 5 cm from the inlet into the chamber by means of an optical spectrometer. The intensity of this UV line for argon depends on the density of the resonant states that emit these photons. The density of these states is obtained by optical absorption measurements: the higher the absorption, the higher the UV intensity emitted. The most direct way to optimize UV emission in the case of a single gas such as pure argon is to cause the pressure to vary. FIG. 13 shows in fact that the pressure at which maximum UV intensities are observed depends on the flow rate of argon. If the latter is low (e.g. 70 mslm), the operating pressure is preferably low (here about 0.1 torr). On the contrary, if it is high, the optimal pressure is preferably higher. The survival curve of the B. subtilis spores is represented in FIG. 13 and confirms the results of FIG. 4. By adjusting the pressure and the flow rate of argon, it is possible to have a higher yield of UV emission intensity, which makes it possible to achieve sterilization in a shorter period of time. The results reported in FIG. 13 show the survival curve of B. subtilis spores in a post-discharge of pure argon, as obtained in the conditions indicated, and in the presence of an intensity of UV emission close to a maximum value.

A third sterilizer (not illustrated), in accordance with the present invention, of parallelepipedal structure and made of aluminum, and having a capacity of 60 liters, is supplied with a plasma produced at 200 MHz in a tube whose inner diameter is 48 mm. The results obtained are comparable to those collected with a 50 liter parallelepipedal sterilizer operating at 915 MHz. To increase the uniformity of distribution of the active species in the sterilization chamber, the latter is supplied from two plasma sources, which are ideally separated from one another. On the other hand, the orifice of evacuation for the gases is placed, in the present case, in the axis of the chamber, while in FIG. 6 pumping is carried out at the bottom of the chamber.

It has thus been shown that by controlling the flow rate and/or the gas pressure in the chamber, it is possible to maximize the Ultra Violet (UV) radiation intensity once a given range of pressure and/or gas flow has been chosen. Moreover, It has been found that for the same sterilization chamber, and for the same frequency, the surface of the objects to be sterilized may be increased considerably through a selection of certain structural and energetic parameters of the system. It also has been shown that the axial homogeneity of the plasma is influenced by the flow rate and pressure, as well as the feed gas that is used to produce the plasma. It also has been found that the transverse and axial homogeneity of the plasma flow is dependent on a structural ratio R, which is indicative of the difference of size of the discharge tube with respect to that of the sterilization chamber, R is hereinafter defined. To increase transverse homogeneity, for example, the ratio R must be increased. The upper limit of ratio R can be determined by the diameter of the discharge tube that is used. The maximum diameter of the discharge tube can be increased when the frequency of the electric field is decreased. On the other hand, there is a lower limit of frequency of the electric field with respect to the efficiency of HF power transfer towards the discharge. Consequently, it is advantageous to harmonize tube diameter and plasma source frequency so as to obtain the highest homogeneity possible of the sterilizing species.

Moreover, it has been shown that by using a gas stream consisting of argon it is possible to obtain sterility of the contaminated object and that such a treatment avoids to expose the contaminated object to oxidizing species so that deterioration or erosion of the object is considerably reduced.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. Process for sterilizing a contaminated object, comprising:
   inserting the object in a sterilization chamber having at least one discharge tube in communication therewith,
   feeding the tube with a liquid or gaseous stream, and submitting the stream to an electric field so as to generate a plasma, thereby exposing said contaminated object to the action of sterilizing species that are present in a post-discharge zone or in a zone of excitation of said plasma,
   measuring at least one of UV emission intensity and optical absorption due to a density of resonant states of UV photon species in the sterilization chamber as a function of gas pressure to determine a gas pressure that maximizes UV radiation intensity and that maximizes the presence of UV photon emitting species in the sterilization chamber,
   measuring at least one of UV emission intensity and optical absorption due to a density of resonant states of UV photon species in the sterilization chamber as a function of stream flow rate to determine a flow rate that maximizes UV radiation intensity and that maximizes the presence of UV photon emitting species in the sterilization chamber, and
   applying the stream at a flow rate and a gas pressure in the sterilization chamber that maximizes UV radiation intensity and the presence of UV photon emitting species in the sterilization chamber.

2. Process according to claim 1, wherein the gas stream consists of helium, neon, argon, krypton, xenon, or a mixture thereof.

3. Process according to claim 1, wherein the gas stream consists of argon.

4. Process according to claim 1, wherein the object is contaminated with micro-organisms selected from the group consisting of viruses, spores, bacteria, fungi, molds and prions.

5. Process according to claim 1, wherein the electric field frequency is from 10 Megahertz to 3 Gigahertz.

6. Process according to claim 5, wherein said frequency is from 100 to 2450 MHz.

7. Process according to claim 1, wherein the gas stream flow rate has a value that is comprised between 10 and 5000 standard $cm^3$ per minute.

8. Process according to claim 7, wherein the gas stream flow rate is comprised between 50 and 3000 standard $cm^3$ per minute.

9. Process according to claim 1, wherein the pressure generated inside the sterilization chamber is between 0.05 and 10 torrs.

10. Process according to claim 1, wherein the gas stream comprises argon and the pressure generated inside the sterilization chamber is between 0.1 and 4 torrs.

11. Process according to claim 1, wherein the gas stream comprises at least one component selected from the group consisting of molecular oxygen, nitrogen, neon, argon, krypton, xenon, helium, oxygen, carbon monoxide, carbon dioxide, $N_2O$, gases of formula $NO_x$ wherein x represents 1, 2 or 3, air, and mixtures thereof.

12. Process according to claim 11, wherein the gas stream comprises molecular oxygen.

13. Process according to claim 12, wherein the gas stream comprises at least 0.04% of molecular oxygen.

14. Process according to claim 12, wherein the gas stream comprises from 0.1 to 10% of molecular oxygen.

15. Process of sterilization according to claim 11, wherein the gas stream comprises nitrogen, argon and helium, in addition to molecular oxygen.

16. Process of sterilization according to claim 11, wherein the gas stream comprises nitrogen, argon and nitrogen dioxide, in addition to molecular oxygen.

17. Process according to claim 1, wherein the gas stream comprises molecular oxygen and a component selected from the group consisting of nitrogen, neon, argon, krypton, xenon, helium, oxygen, carbon monoxide, carbon dioxide, $N_2O$, gases of formula $NO_x$ wherein x represents 1, 2 or 3, air, and mixtures thereof.

18. Process according to claim 1, wherein the steps involve a pulsed gas in an electric field that is applied continuously, a pulsed electric field in a continuous gas stream, a pulsed gas in a synchronously pulsed electric field, a gas change; or a combination of these steps.

19. Process according to claim 1, wherein the ratio R=(CDT)/(CSC) is comprised between 0.01 and 0.70, where CDT represents the cross-section of the discharge tube or the sum of the cross-sections of the discharge tubes, and CSC represents the cross-section of the sterilization chamber.

20. Process according to claim 1, wherein said contaminated object is exposed to the action of sterilizing species that are present in a post-discharge zone said plasma.

21. Process according to claim 1, wherein
   optical absorption due to a density of resonant states of UV photon emitting species is measured in the sterilization chamber as a function of gas pressure to determine a gas pressure that maximizes UV radiation intensity and that maximizes the presence of UV photon emitting species in the sterilization chamber,
   optical absorption due to a density of resonant states of UV photon emitting species is measured in the sterilization chamber as a function of stream flow rate to determine a flow rate that maximizes UV radiation intensity and that maximizes the presence of UV photon emitting species in the sterilization chamber, and
   the stream is applied at a flow rate and a gas pressure in the sterilization chamber that maximizes UV radiation intensity and that maximizes the presence of UV photon emitting species in the sterilization chamber.

22. Process for sterilizing a contaminated object in a sterilization chamber provided with at least one discharge tube, wherein the discharge tube(s) is in communication with the sterilization chamber and is (are) supplied with a liquid or gas stream, the contaminated object is subjected in the sterilization chamber to the action of sterilizing species that are present in a post-discharge zone or in the excitation zone of the plasma that is generated at the level of the discharge tube(s) by passing the stream in an electric field, wherein the ratio R=(CDT)/(CSC), in which CDT represents the cross-section of the discharge tube in communication with the sterilization chamber or the sum of the cross-sections of the discharge tube(s), and CSC represents the cross-section of the sterilization chamber, confirms the relation 0.05<R<0.70, and wherein the stream is adjusted by measuring at least one of UV emission intensity and optical absorption due to a density of resonant states of UV photon species in the sterilization chamber as a function of gas pressure to determine a gas pressure that maximizes UV radiation intensity and that maximizes the presence of UV photon emitting species in the sterilization chamber, measuring at least one of UV emission intensity and optical absorption due to a density of resonant states of UV photon species in the sterilization chamber as a function of stream flow rate to determine a flow rate that maximizes UV radiation intensity and that maximizes the presence of UV photon emitting species in the sterilization chamber, and applying the stream at a flow rate and a gas pressure in the sterilization chamber that maximizes UV radiation intensity and the presence of UV photon emitting species in the sterilization chamber.

23. Process according to claim 22, wherein $0.09 \leq R \leq 0.60$.

24. Process according to claim 22, wherein $0.2 \leq R \leq 0.40$.

25. Process according to claim 22, wherein the gas stream flow rate has a value that is comprised between 10 and 5000 standard cm$^3$ per minute.

26. Process according to claim 25, wherein the gas stream flow rate is comprised between 50 and 3000 standard cm$^3$ per minute.

27. Process according to claim 22, wherein the pressure generated inside the sterilization chamber is between 0.05 and 10 torrs.

28. Process according to claim 22, wherein the gas stream comprises argon and the pressure generated inside the sterilization chamber is between 0.1 and 4 torrs.

29. Process according to claim 22, wherein the gas stream consists of helium, neon, argon, krypton, xenon, or a mixture thereof.

30. Process according to claim 22, wherein the gas stream consists of argon.

31. Process according to claim 22, wherein the gas stream comprises at least one component selected from the group consisting of molecular oxygen, nitrogen, neon, argon, krypton, xenon, helium, oxygen, carbon monoxide, carbon dioxide, N$_2$O, gases of formula NO$_x$ wherein x represents 1, 2 or 3, air, and mixtures thereof.

32. Process according to claim 22, wherein the gas stream comprises molecular oxygen and a component selected from the group consisting of nitrogen, neon, argon, krypton, xenon, helium, oxygen, carbon monoxide, carbon dioxide, N$_2$O, gases of formula NO$_x$ wherein x represents 1, 2 or 3, air, and mixtures thereof.

33. Process according to claim 32, wherein the gas stream comprises from 0.1 to 10% of molecular oxygen.

34. Process according to claim 22, wherein the gas stream comprises N$_2$ and molecular oxygen, the percentage of molecular oxygen in the stream being adjusted to a content x, of molecular oxygen, such that $0<x<0.5\%$.

35. Process according to claim 34, wherein x is varying from 0.1 to 0.4%.

36. Process according to claim 34, wherein the molecular oxygen is at least partially converted into atomic oxygen.

37. Process according to claim 22, wherein the sterilization chamber is perpendicular to the direction of the gas stream feeding the discharge tube and cross-section (CSC) representing the cross-section of the chamber in communication with the discharge tube and which is perpendicular to the plasma current.

38. A device allowing the implementation of the process defined in claim 22, comprising a source of plasma associated with one of the walls of the sterilization chamber by means of at least one discharge tube in which there is injected a gas or a mixture of gases eventually producing the plasma, the chamber comprising the object to be sterilized, and a vacuum pump to carry the gases in the chamber and to maintain therein a reduced pressure, wherein the source of plasma comprises an electric field applicator and the ratio R=(CDT)/(CSC), in which (CDT) represents the cross-section of the discharge tube or the sum of the cross-sections of the discharge tube(s) in contact with the sterilization chamber and (CSC) represents the cross-section of the sterilization chamber (CSC), confirming the relation 0.05<R<0.70.

39. Process according to claim 22, wherein optical absorption due to a density of resonant states of UV photon emitting species is measured in the sterilization chamber as a function of gas pressure to determine a gas pressure that maximizes UV radiation intensity and that maximizes the presence of UV photon emitting species in the sterilization chamber, optical absorption due to a density of resonant states of UV photon emitting species is measured in the sterilization chamber as a function of stream flow rate to determine a flow rate that maximizes UV radiation intensity and that maximizes the presence of UV photon emitting species in the sterilization chamber, and the stream is applied at a flow rate and a gas pressure in the sterilization chamber that maximizes UV radiation intensity and that maximizes the presence of UV photon emitting species in the sterilization chamber.

* * * * *

UNITED STATES PATENT AND TRADEMARK OFFICE
CERTIFICATE OF CORRECTION

PATENT NO. : 7,695,673 B2
APPLICATION NO. : 11/044998
DATED : April 13, 2010
INVENTOR(S) : M. Moisan et al.

It is certified that error appears in the above-identified patent and that said Letters Patent is hereby corrected as shown below:

| COLUMN | LINE | ERROR |
|---|---|---|
| 14 (Claim 20, | 40 line 3) | "post-discharge zone said plasma." should read --post-discharge zone of said plasma-- |

Signed and Sealed this

Twelfth Day of October, 2010

David J. Kappos
*Director of the United States Patent and Trademark Office*